US010190990B2

United States Patent
Dehkordi et al.

(10) Patent No.: US 10,190,990 B2
(45) Date of Patent: Jan. 29, 2019

(54) LED-BASED FIBER PROPERTY MEASUREMENT

(71) Applicant: Uster Technologies AG, Uster (CH)

(72) Inventors: Peyman Dehkordi, Knoxville, TN (US); Weichang Zhao, Oak Ridge, TN (US); Youe-Tsyr Chu, Knoxville, TN (US); Daniel J Rairigh, Knoxville, TN (US); Hossein M. Ghorashi, Knoxville, TN (US); C. Roger Riley, Knoxville, TN (US); Kent A. Rinehart, Knoxville, TN (US)

(73) Assignee: Uster Technologies, AG, Uster (CH)

( * ) Notice: Subject to any disclaimer, the term of this patent is extended or adjusted under 35 U.S.C. 154(b) by 9 days.

(21) Appl. No.: 15/561,233

(22) PCT Filed: Mar. 23, 2016

(86) PCT No.: PCT/CH2016/000049
§ 371 (c)(1),
(2) Date: Sep. 25, 2017

(87) PCT Pub. No.: WO2016/149848
PCT Pub. Date: Sep. 29, 2016

(65) Prior Publication Data
US 2018/0052116 A1 Feb. 22, 2018

Related U.S. Application Data

(60) Provisional application No. 62/137,495, filed on Mar. 24, 2015, provisional application No. 62/211,369, filed on Aug. 28, 2015.

(51) Int. Cl.
*G01N 21/27* (2006.01)
*G01N 21/88* (2006.01)
(Continued)

(52) U.S. Cl.
CPC ......... *G01N 21/8806* (2013.01); *G01N 21/27* (2013.01); *G01N 21/8915* (2013.01);
(Continued)

(58) Field of Classification Search
CPC ............... G01N 21/8806; G01N 21/27; G01N 21/8915; G01N 33/36; G01N 2201/061; G01N 2201/0627
See application file for complete search history.

(56) References Cited

U.S. PATENT DOCUMENTS 5,130,559 A * 7/1992 Leifeld ................ D01G 31/003
19/65 A
5,229,841 A 7/1993 Taranowski et al.
(Continued)

FOREIGN PATENT DOCUMENTS

CN 103344337 10/2013
DE 3706056 5/1988
(Continued)

*Primary Examiner* — Dominic J Bologna
(74) *Attorney, Agent, or Firm* — Luedeka Neely Group, P.C.; Rick Barnes

(57) ABSTRACT

The apparatus is for measuring at least one of color and trash in a fiber sample. A light emitting diode light source generates an incident light that is directed toward the fiber sample, and reflected by the fiber sample, thereby producing a reflected light. A sensor receives the reflected light and produces a signal. A controller controls the light source and the sensor, and at least one of receives and adjusts the signal. At least one of the incident light, the reflected light and the signal is conditioned to compensate for differences between the light emitting diode light source and a xenon light source. Thus, drawbacks of the xenon light source used to date can be avoided.

19 Claims, 3 Drawing Sheets

(51) Int. Cl.
*G01N 21/89* (2006.01)
*G01N 33/36* (2006.01)

(52) U.S. Cl.
CPC ....... *G01N 33/36* (2013.01); *G01N 2201/061* (2013.01); *G01N 2201/0627* (2013.01)

(56) References Cited

U.S. PATENT DOCUMENTS

| | | | |
|---|---|---|---|
| 5,530,551 A * | 6/1996 | Cantrall | G01B 11/105 356/335 |
| 5,745,176 A * | 4/1998 | Lebens | G01N 21/8806 235/462.42 |
| 5,915,279 A * | 6/1999 | Cantrall | G01B 11/105 250/559.11 |
| 6,040,905 A * | 3/2000 | Cheng | G01N 21/8915 209/509 |
| 6,052,182 A * | 4/2000 | Irick, Sr. | G01N 21/8915 356/238.1 |
| 6,175,408 B1 | 1/2001 | Henze | |
| 6,201,602 B1 | 3/2001 | Bouvyn | |
| 6,202,493 B1 | 3/2001 | Cantrall et al. | |
| 6,380,548 B1 * | 4/2002 | Henze | D01H 13/26 250/559.4 |
| 6,452,157 B1 | 9/2002 | Hosel | |
| 6,771,365 B1 * | 8/2004 | Pirani | G01N 21/8915 356/238.2 |
| 6,912,048 B2 | 6/2005 | Pirani et al. | |
| 7,050,160 B1 * | 5/2006 | Johnson | G01B 7/06 356/630 |
| 7,333,203 B2 | 2/2008 | Ott | |
| 3,045,168 A1 | 10/2011 | Missotten | |
| 8,199,319 B2 * | 6/2012 | Baxter | G01N 21/84 356/402 |
| 9,970,750 B2 * | 5/2018 | Akagi | G01B 11/245 |
| 2004/0119972 A1 * | 6/2004 | Smit-Kingma | D06F 39/003 356/238.1 |
| 2009/0002707 A1 * | 1/2009 | Berger | G01N 21/8915 356/430 |
| 2015/0089751 A1 * | 4/2015 | Landa | B65D 1/0223 8/406 |
| 2016/0054281 A1 * | 2/2016 | Smeeton | G01N 21/532 250/373 |

FOREIGN PATENT DOCUMENTS

| | | | |
|---|---|---|---|
| DE | 19534517 | 3/1997 | |
| EP | 1808690 A1 * | 7/2007 | ......... G01N 21/8915 |
| WO | 8203688 | 10/1982 | |
| WO | 2009065451 | 5/2009 | |

* cited by examiner

LED-BASED FIBER PROPERTY MEASUREMENT

This application claims rights and priority on prior pending PCT application serial number PCT/CH2016/000049 filed 2016 Mar. 23, which claims priority on U.S. provisional patent application Ser. No. 62/137,495 filed 2015 Mar. 24 and U.S. provisional patent application Ser. No. 62/211,369 filed 2015 Aug. 28, the entirety of the disclosures of which are incorporated herein by reference.

FIELD

This invention relates to the field of measuring the properties of textile fibers using optoelectronics. More specifically, it relates to measuring color and non-lint content (referred to as trash) of a fiber sample while matching an existing reference standard that has been established worldwide.

INTRODUCTION

Historically, color and trash measurements for fibers such as cotton were performed by human classers. More recently, the standards for such classing have been established and measured by USTER® High Volume Instrument (HVI), as described in the brochure "USTER® HVI 1000—The fiber classification and analysis system", Uster Technologies AG, 2013. The current USTER® HVI 1000 instrument uses a xenon light source to illuminate the fiber sample, thereby making any trash within the sample and the color of the sample visible for image capture and analysis.

WO-99/22225 A1 (Fiber Quality Monitor) describes certain aspects of the current cotton-classing system that uses a xenon illumination source. WO-00/08448 A1 (Fiber Color Grading System) describes other aspects of that cotton-classing system. The entirety of those disclosures are incorporated herein by reference.

Xenon light sources tend to degrade over time, until eventually they must be replaced. Although there are light sources besides xenon, classing is an extremely sensitive operation, and xenon illumination has become the standard in the classing industry.

What is needed, therefore, is a system that reduces issues such as those described above, at least in part.

SUMMARY

The above and other needs are met by an apparatus for measuring at least one of color and trash in a fiber sample. A light emitting diode light source generates an incident light that is directed toward the fiber sample, and reflected by the fiber sample, thereby producing a reflected light. A sensor receives the reflected light and produces a signal. A controller controls the light source and the sensor, and at least one of receives and adjusts the signal. The apparatus further comprises means for conditioning at least one of the incident light, the reflected light, and the signal to compensate for differences between the light emitting diode light source and a xenon light source.

In various embodiments according to this aspect of the invention, the means for conditioning the incident light comprise at least one beam shaping device and/or at least one optical filter disposed between the light source and the fiber sample. In some embodiments, the means for conditioning the reflected light comprise at least one optical filter disposed between the fiber sample and the sensor. In some embodiments, the means for conditioning the signal comprise a digital signal processor.

In some embodiments, the sensor is at least one of a spectrometer, a photomultiplier tube, a photodiode, and a charge-coupled device.

In some embodiments, the apparatus further comprises at least one reference light emitting diode monitored by the controller, for capturing the signal when the reference light emitting diode is at a predetermined brightness. In some embodiments, the at least one reference light emitting diode is separate and distinct from the light source. In some embodiments, the at least one reference light emitting diode is part of the light source. In some embodiments, the at least one reference light emitting diode does not illuminate the fiber sample. In some embodiments, the apparatus further comprises means for conditioning light from the at least one reference light emitting diode prior to being sensed.

Some embodiments include first and second reference light emitting diodes that are monitored by the controller, for capturing the signal when the first and second reference light emitting diodes are at predetermined brightnesses, wherein the means for conditioning light from the first and second reference light emitting diodes are configured for separately conditioning light from the first and second reference light emitting diodes prior to being sensed.

In some embodiments, the means for conditioning are settable with different parameters depending at least in part upon whether a color measurement is to be taken or a trash measurement is to be taken.

A preferred embodiment of the apparatus for measuring at least one of color and trash in a fiber sample comprises a light emitting diode light source for generating an incident light that is directed toward the fiber sample and reflected by the fiber sample, thereby producing a reflected light, a sensor for receiving the reflected light and producing a signal, a controller for controlling the light source and the sensor, and at least one of receiving and adjusting the signal, optics disposed between the light source and the fiber sample to condition the incident light, and filters disposed between the fiber sample and the sensor to condition the reflected light. The conditioning compensates for differences between the light emitting diode light source and a xenon light source.

According to another aspect of the invention there is described a method for measuring at least one of color and trash in a fiber sample, by using a light emitting diode light source to generate an incident light that is directed toward the fiber sample, and reflected by the fiber sample, thereby producing a reflected light. The reflected light is received with a sensor that produces a signal. The light source and the sensor are controlled, and the signal is at least one of received and adjusted. At least one of the incident light, the reflected light and the signal are conditioned to compensate for differences between the light emitting diode light source and a xenon light source.

In some embodiments, the incident light is conditioned using at least one beam shaping device and/or at least one optical filter disposed between the light source and the fiber sample. In some embodiments, the reflected light is conditioned using at least one optical filter disposed between the fiber sample and the sensor. In some embodiments, the signal is conditioned using a digital signal processor.

In some embodiments, at least one reference light emitting diode is monitored with a controller, and the signal is captured when the at least one reference light emitting diode is at a predetermined brightness.

In some embodiments, the conditioning is set with different parameters depending at least in part upon whether a color measurement is to be taken or a trash measurement is to be taken.

In a preferred embodiment of the method according to the invention, the incident light is conditioned using optics disposed between the light source and the fiber sample. The reflected light is conditioned using filters disposed between the fiber sample and the sensor. The conditioning compensates for differences between the light emitting diode light source and a xenon light source.

DRAWING

Further advantages of the invention are apparent by reference to the detailed description when considered in conjunction with the figures, which are not to scale so as to more clearly show the details, wherein like reference numbers indicate like elements, and which depict:

DESCRIPTION

With current advancements in solid state lighting, there are now opportunities to replace xenon light sources with more advanced lighting sources, such as light emitting diodes (collectively referred to herein as LEDs, and including other similar devices such as OLEDs). A light-emitting diode is a two-lead semiconductor light source. It is a p-n junction diode, which emits light when activated. When a suitable voltage is applied to the leads, electrons are able to recombine with electron holes within the device, releasing energy in the form of photons. This effect is called electroluminescence. The color of the light (or its wavelength, corresponding to the energy of the photon) is determined by the energy band gap of the semiconductor.

LED technologies offer more repeatable optical energy at a precise wavelength with a longer lifetime. While LEDs seem to be a simple replacement for xenon, they exhibit a new set of challenges for fiber color and trash measurements.

In order to match the exact color and trash values of the standards that are set by xenon illumination, an instrument using an LED light source must measure color and trash for a given sample to match exactly the measurements taken by a xenon based instrument. Unfortunately, LED light sources do not have the same spectral or electrical characteristics as xenon light sources, and merely replacing xenon light sources with LED light sources has not been satisfactory.

Figure 2:
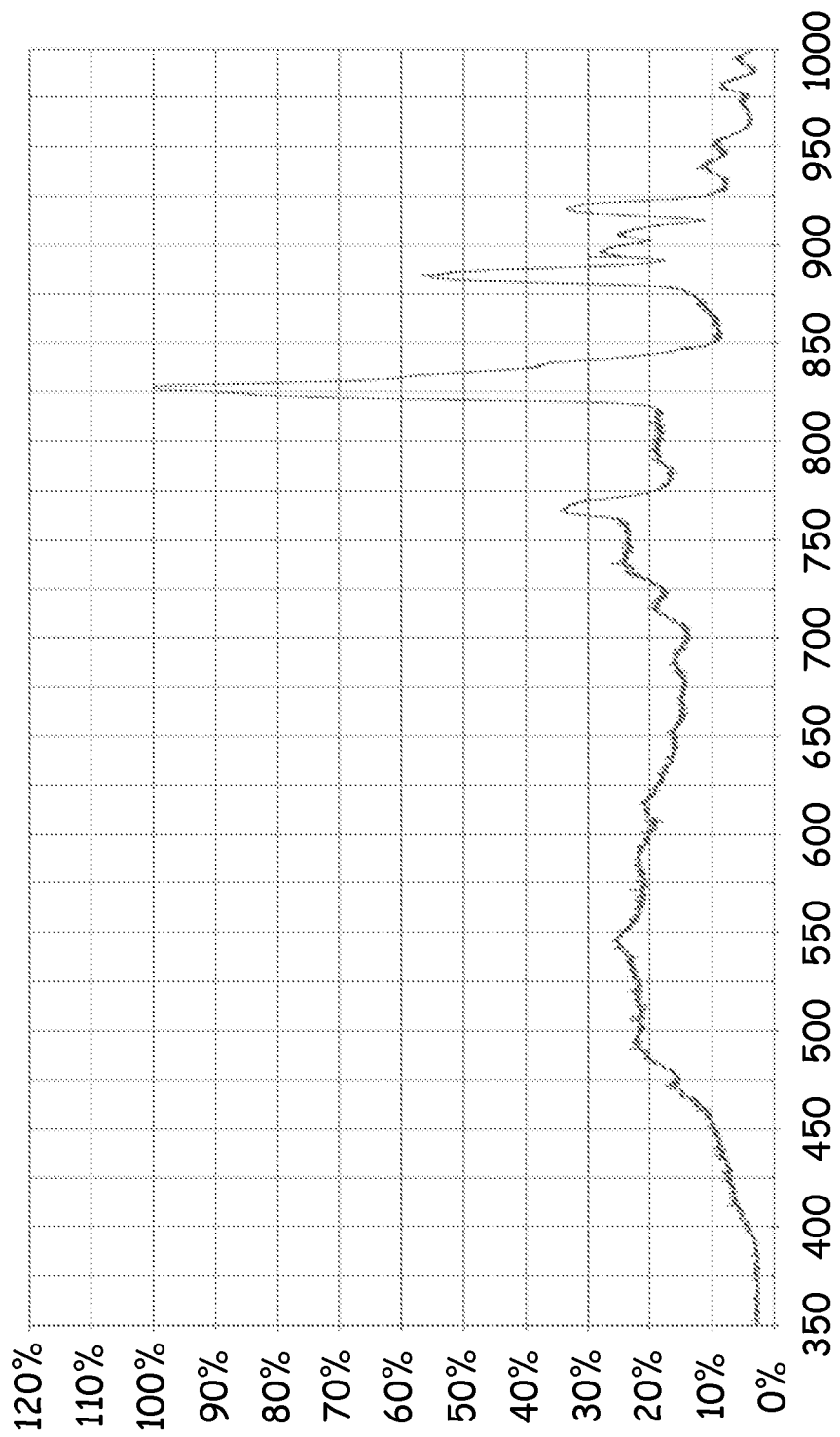
FIG. 2 is a typical spectral density plot for a xenon light source.
Figure 3:
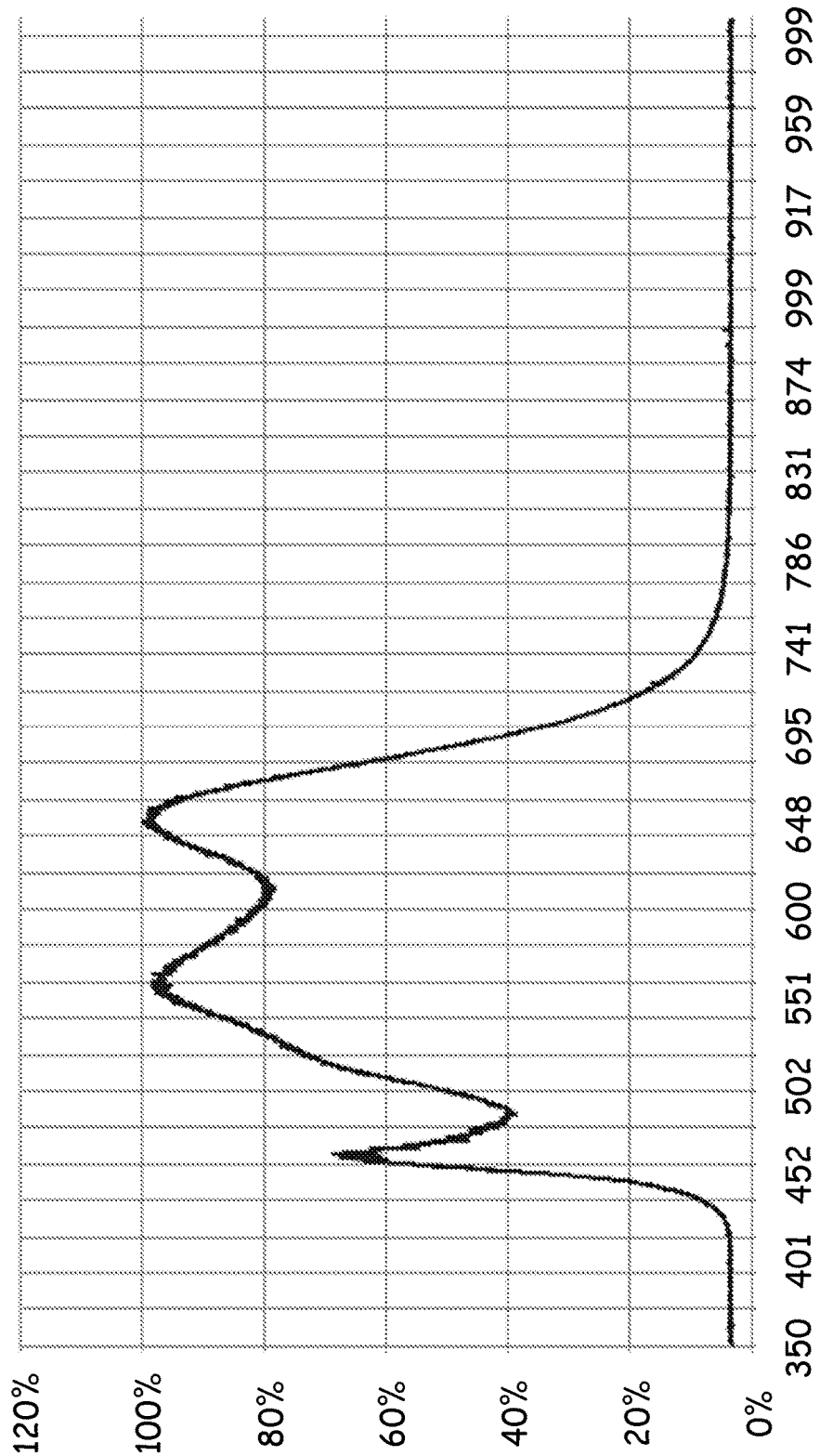
FIG. 3 is a typical spectral density plot for an LED light source.

FIG. 2 depicts a typical spectral density plot, i.e., a spectral power distribution $F_x(\lambda)$, for a xenon light source, which represents the spectral topography that is desired from the LED source. FIG. 3 depicts a typical spectral density plot, i.e., a spectral power distribution $F_x(\lambda)$, for a white LED light source, namely, XENOLED™ AT56SNW-A4000 from ALLIX, South Korea. As can be seen, the two topographies are very different, one from another, and yet an apparatus according to an embodiment of the present invention is to produce and interpret an image or signal based on a fiber sample that classes the fiber sample over a desired range of wavelengths $\lambda$ as described herein, according to the standards that have been developed using xenon light sources.

For example, problems that have had to be overcome in the present embodiments include matching (1) the exact spectral response of xenon in the region of the color and trash measurements, (2) a similar beam angle as xenon, and (3) similar light distribution uniformity over the fiber surface as a xenon source. Thus, various embodiments of the present invention include an innovative way of using LED technologies for fiber color and trash measurements, which address the above-mentioned challenges of backward compatibility to xenon.

Overview

Figure 1:
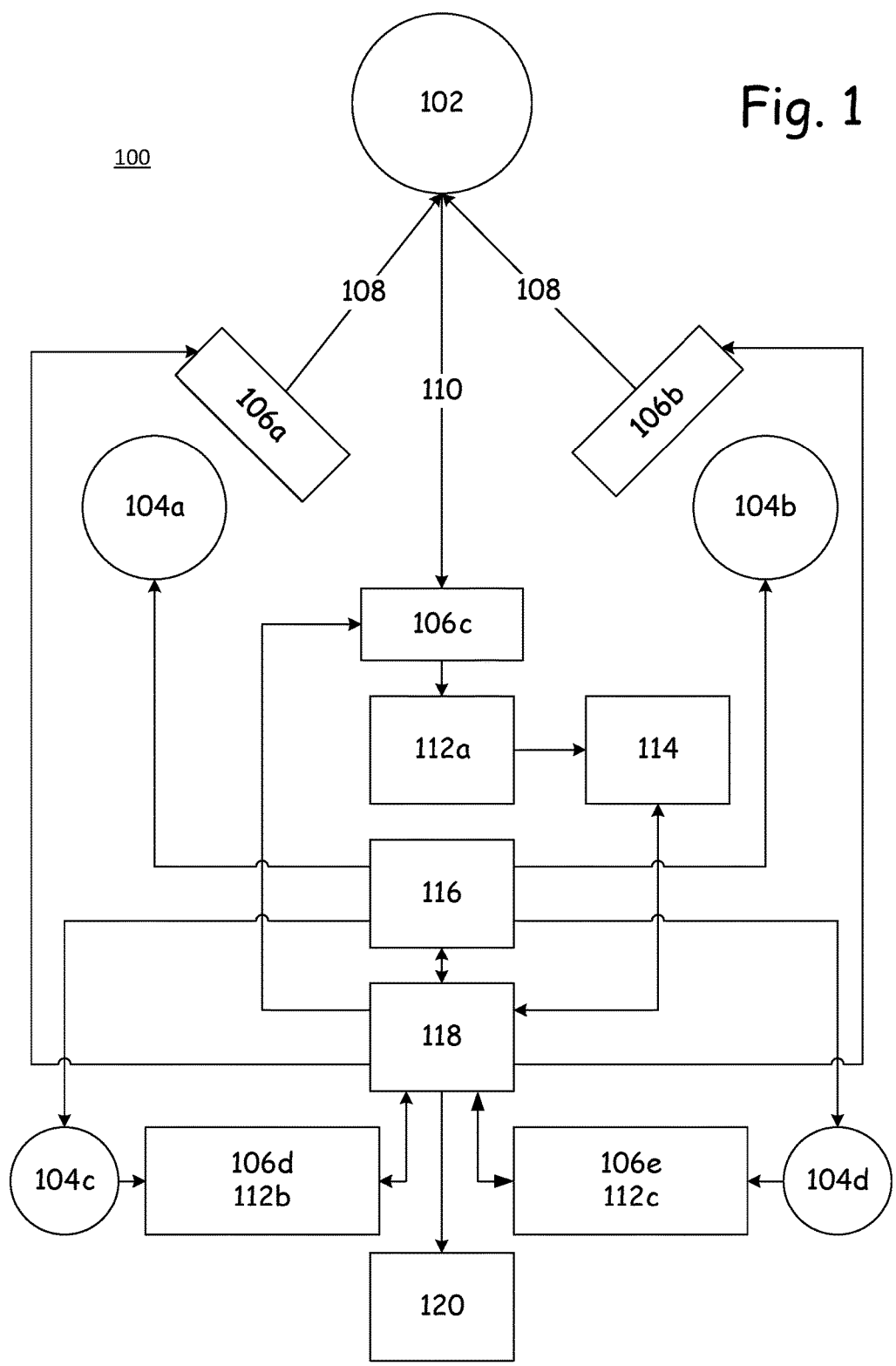
FIG. 1 is a functional block diagram of an instrument according to an embodiment of the present invention.

With reference now to FIG. 1, there is depicted a functional block diagram of various elements of a system or apparatus 100 according to an embodiment of the invention. The apparatus 100 as depicted includes an array of lamps 104a, 104b, such as LEDs. In the embodiment depicted, only two such lamps 104a, 104b are depicted, but it is appreciated that in most embodiments, many lamps 104 will be implemented. Some embodiments use an LED array with one of either a primary peak in or a flat output throughout the range of 380 nm and 800 nm.

The incident light 108 produced by the lamps 104a, 104b is conditioned by conditioners 106a, 106b in some embodiments. The conditioners 106a, 106b are placed over all of the lamps 104a, 104b in some embodiments, and only some of the lamps 104 in other embodiments. In some embodiments the conditioners 106a, 106b take the form of optics that shape the incident light 108. In other embodiments the conditioners 106a, 106b take the form of filters that filter the incident light 108. In some embodiments the filters or optics are set optical devices, and in other embodiments the filters or optics are adjustable or changeable, such as under the control of a controller 118.

The incident light 108 is received and reflected by a fiber sample 102, thereby producing reflected light 110. In some embodiments the fiber sample 102 is a cotton fiber sample. In other embodiments the fiber sample 102 is some other natural fiber sample. In some embodiments, the fiber sample 102 is a sample of synthetic fibers, such as polyester. In other embodiments, the fiber sample 102 is a combination of fibers such as those described above.

In some embodiments the reflected light 110 passes through a third conditioner 106c before encountering a main sensor 112a. The third conditioner 106c, in some embodiments, takes various forms such as those described above. In some embodiments the conditioners 106a-106c are implemented so as to make the light 108 or 110 have properties similar to those of xenon light sources such as, for example, color shaping. In some embodiments only the first conditioner 106a and the second conditioner 106b are used to condition the incident light 108, and in some embodiments only the third conditioner 106c is used to condition the reflected light 110, and in some embodiments all of the conditioners 106a, 106b, and 106c are used to condition both the incident light 108 and the reflected light 110.

The incident light 110 is received by the main sensor 112a, which in some embodiments is a color sensor, so that both fiber color and trash color of the fiber sample 102 can be detected directly by the main sensor 112a. In various embodiments the main sensor 112 is at least one of a photomultiplier tube, a charge coupled device, a photodiode, and a spectrometer. The main sensor 112a produces a signal that in some embodiments is output to a converter 114, so as to convert an analog signal to a digital signal. The converter 114, if present in the given embodiment, then outputs the digital signal to the controller 118. In other embodiments, the main sensor 112a outputs a digital signal directly to the controller 118.

The controller 118 controls the various components of the apparatus 100, as described above and elsewhere herein. For example, the controller 118 controls the firing of the lamps 104a, 104b, such as through a driver 116. In some embodiments the driver 116, under control of the controller 118, creates different illumination patterns for the lamps 104a, 104b. For example, some of the lamps 104a, 104b may be illuminated in certain situations, and all of the lamps 104a, 104b may be illuminated in other situations.

The driver 116, in some embodiments, controls ramping patterns for the lamps 104a, 104b, such as by bringing them up to a desired illumination at a specific rate, holding the illumination level for a given period of time, and then decreasing the level of illumination at a given rate. This can be accomplished either by powering all of the lamps 104a, 104b at a given power or power ramp, or by powering different lamps 104a, 104b at different times or at different rates, depending upon the embodiment.

In some embodiments a first reference lamp 104c is powered with some of the other lamps 104a or 104b or all, and its light is received as direct illumination either by a first dedicated sensor 112b and an optional fourth conditioner 106d, or by the main sensor 112a and the optional third conditioner 106c. In some embodiments the signal from the first dedicated sensor 112b or from the main sensor 112a as a measure for the light intensity delivered by the first reference lamp 104c is output to the controller 118, and any images of the fiber sample 102 gathered by the main sensor 112a are associated with an intensity value of the first reference lamp 104c. In some embodiments no image of the fiber sample 102 is captured until the first reference lamp 104c is at a given desired intensity value. In some embodiments the first reference lamp 104c is blocked from illuminating the fiber sample 102 in any way. In some embodiments the first reference lamp 104c is of the same type and age as the other lamps 104a and 104b.

In some embodiments a second reference lamp 104d is employed, that is sensed by a second dedicated sensor 112c and an optional fifth conditioner 106e.

In some embodiments the lamps 104a-104d are pulsed to a light-emitting intensity that is above the desired threshold at which an image is to be taken of the fiber sample 102, and then the brightness is monitored during the decay of the light intensity, and the image is captured as the light intensity descends to the desired value. In another embodiment, the lamps 104a-104d are energized to a steady level, the measurement is taken by capturing an image, the lamps 104a-104d are turned off, and a ratio is used to normalize the measurement signal from the lamps 104a and 104b to the reference signal from the reference lamps 104c and/or 104d to compensate for variations in LED light output from effects such as temperature or aging.

In some embodiments all of the sensors 112a-112c are of the same type, and in other embodiments some or all of the sensors 112a-112c are of different types, as described elsewhere herein. In some embodiments all of the conditioners 106a-106e are of the same type, and in other embodiments some or all of the conditioners 106a-106e are of different types, as described elsewhere herein. Some embodiments do not use all of the lamps 104a-104d or conditioners 106a-106e or sensors 112a-112c as depicted in the FIG. 1.

In some embodiments, one of the reference lamps 104c is used during color measurements, while the other reference lamp 104d is used during trash measurements. In other embodiments both of the reference lamps 104c and 104d are used during both color measurements and trash measurements.

The controller 118 sends the captured images, and any metadata such as the intensity of the reference lamps 104c, 104d, to other systems 120 or other portions of the apparatus 100 that are embodied in FIG. 1 as system 120, such as to storage, memory, a personal computer, a user interface, across a network connection, and so forth.

The conditioners 106a-106e are selected, and in some embodiments controlled by the controller 118, so as to make at least one of the characteristics of the incident light 108 or the reflected light 110 at least similar to if not substantially the same as those of xenon light sources. The reason for this is that various light sources have different characteristics, and all of the standards for fiber color and fiber trash measurement have now been standardized on xenon light sources. Thus, various embodiments of the present invention combine the benefits of LED light sources with color and trash measurement, while enabling backward comparison and compatibility with the standards that have been set for xenon light sources, and even earlier standards.

Without being bound by any particular theory, the following additional concepts are presented.

Color Measurement

In order for the LED system to measure the fiber color properly, it should match the xenon system spectral response. The spectral response of the xenon system may be described as follows:

$$F_{color}(\lambda) = F_x(\lambda) \cdot F_s(\lambda) \cdot F_f(\lambda) \cdot F_d(\lambda)$$

for $\lambda_{min} < \lambda < \lambda_{max}$ (wavelength region of interest for fiber color measurement), where:
$F_x(\lambda)$=Spectral response of xenon light source,
$F_s(\lambda)$=Spectral response of the sample,
$F_f(\lambda)$=Spectral response of the optical conditioner,
$F_d(\lambda)$=Spectral response of the detector, and
$F_{color}(\lambda)$=Spectral response of overall system for color measurement.

Similarly, the spectral response of the LED system may be described as follows:

$$F_{color}(\lambda) = F_l(\lambda) \cdot F_s(\lambda) \cdot F_f(\lambda) \cdot F_d(\lambda)$$

for $\lambda_{min} < \lambda < \lambda_{max}$ (wavelength region of interest for fiber color measurement), where:
$F_l(\lambda)$=Spectral response of LED light source,
$F_s(\lambda)$=Spectral response of the sample,
$F_f(\lambda)$=Spectral response of the optical conditioner,
$F_d(\lambda)$=Spectral response of the detector, and
$F_{color}(\lambda)$=Spectral response of overall system for color measurement.

LED technology inherently generates optical energy in a relatively narrow energy band, whereas xenon has a wide energy band ranging from UV to Near-IR region. Therefore, $F_l(\lambda)$ is much narrower than $F_x(\lambda)$, and thus a simple, direct, xenon to LED replacement is not possible.

One embodiment includes a light source with multiple LEDs with different wavelengths, and mixes their outputs such that:

$$F_x(\lambda) \approx F_{l1}(\lambda) + F_{l2}(\lambda) + F_{l3}(\lambda) + \ldots$$

for $\lambda_{min} < \lambda < \lambda_{max}$ (wavelength region of interest for fiber color measurement), where $F_{li}$=weighted spectral response of each LED for i=1 to n, n being the number of LEDs.

This embodiment can use commercial off-the-shelf LEDs, but requires a careful selection of their wavelengths, and an even more careful balancing of their outputs to achieve the desired xenon-compatible spectral response. This embodiment not only requires multiple LEDs, but also a more complex controller to drive the LEDs.

In another embodiment, a white LED is used. Contrary to common belief, white LEDs are not really white. These LEDs are typically based on two different operational methods. In the first method, there are multiple LEDs (such as red, green, blue) inside the white LED package, which when combined generate the perceived white color. This embodiment might lack a true white color, and might not match the xenon spectrum well. The second method uses at least one of an ultraviolet, violet, or blue LED, which is placed in a package that is coated with a special phosphor. The interaction of the UV/violet/blue radiation and the phosphor coating fluoresces a lower-energy radiation, the combination of which with the remaining UV/violet/blue radiation results in a white color that typically exhibits a fuller spectrum than the first method. This embodiment is sometimes called "luminescence conversion LED". Different phosphor formulations result in different spectral responses. Therefore, it is possible to formulate a phosphor coating to match the xenon spectral response over the entire wavelength region of interest or in multiple regions of interest:

$$F_x(\lambda) \approx F_l(\lambda)$$

for $\lambda_{min} < \lambda < \lambda_{max}$ (wavelength region of interest for fiber color measurement).

While manipulating the phosphor formulation is an option, it can be expensive and require custom formulation and production for this application.

In another embodiment, commercial, off-the-shelf, white LEDs are used, and matched to the xenon spectrum using optical conditioners. This embodiment might require custom optical conditioner design and fabrication, but may provide a less expensive solution that yields $$F_x(\lambda) \approx F_l(\lambda) \cdot F_f(\lambda)$$

for $\lambda_{min} < \lambda < \lambda_{max}$ (wavelength region of interest for fiber color measurement).

Optical conditioners such as optical filters are well known in technical optics; see, e.g., Handbook of optics, McGraw-Hill, 1978, Sec. 8, "Coatings and Filters", by J. A. Dobrowolski. Various types of optical filters are available, that can change the spectral power distribution of incident electromagnetic radiation at discretion.

Another embodiment uses commercial, off-the-shelf, white LEDs, and matches them to the xenon spectrum using an optical detector with a custom spectral response, given as:

$$F_x(\lambda) \approx F_l(\lambda) \cdot F_d(\lambda)$$

for $\lambda_{min} < \lambda < \lambda_{max}$ (wavelength region of interest for fiber color measurement).

In this embodiment, the detector can be a light sensitive detector such as a photodiode, with a spectral response that is customized to match the xenon spectrum. In some embodiments, the detector is a spectrometer with an output that is digitally processed to match the xenon spectrum in the regions of interest, as:

$$F_x(\lambda) = F_l(\lambda) \cdot [K_1 \cdot F_d(\lambda_1) + K_2 \cdot F_d(\lambda_2) + K_3 \cdot F_d(\lambda_3) + \ldots + K_n \cdot F_d(\lambda_n)]$$

for $\lambda_{min} < \lambda < \lambda_{max}$ (wavelength region of interest for fiber color measurement), where:
$K_1, K_2, K_3 \ldots K_n$ are digital conditioner coefficients to match xenon, and
$\lambda_1, \lambda_2, \lambda_3, \ldots, \lambda_n$ are different wavelengths at which spectrometer outputs are made.

In another embodiment, the embodiments described above are combined to match the xenon spectral response using LED technologies:

$$F_{color}(\lambda) = F_x(\lambda) \cdot F_s(\lambda) \cdot F_f(\lambda) \cdot F_d(\lambda) \approx F_l(\lambda) \cdot F_s(\lambda) \cdot F_f(\lambda) \cdot F_d(\lambda)$$

for $\lambda_{min} < \lambda < \lambda_{max}$ (wavelength region of interest for fiber color measurement).

Trash Measurement

In order for the LED system to measure the fiber trash properly, it should substantially match the xenon system spectral response. The spectral response of the xenon system may be described as follow:

$$F_{trash}(\lambda) = F_x(\lambda) \cdot F_s(\lambda) \cdot F_f(\lambda) \cdot F_d(\lambda)$$

for $\lambda_{min} < \lambda < \lambda_{max}$ (wavelength region of interest for fiber trash measurement), where:
$F_x(\lambda)$=Spectral response of xenon light source,
$F_s(\lambda)$=Spectral response of the sample,
$F_f(\lambda)$=Spectral response of the optical conditioner in front of camera,
$F_c(\lambda)$=Spectral response of the camera, and
$F_{trash}(\lambda)$=Spectral response of overall system for trash measurement.

Similarly, the spectral response of the LED system may be described as follows:

$$F_{trash}(\lambda) = F_l(\lambda) \cdot F_s(\lambda) \cdot F_f(\lambda) \cdot F_d(\lambda)$$

for $\lambda_{min} < \lambda < \lambda_{max}$ (wavelength region of interest for fiber trash measurement), where:
$F_l(\lambda)$=Spectral response of LED light source,
$F_s(\lambda)$=Spectral response of the sample,
$F_f(\lambda)$=Spectral response of the optical conditioner in front of camera,
$F_c(\lambda)$=Spectral response of the camera, and
$F_{trash}(\lambda)$=Spectral response of overall system for trash measurement.

Similar embodiments as described for LED-based color measurement may be incorporated for LED based trash measurement. For example, multiple LEDs with different spectral responses may be combined to match the xenon spectrum. Or the phosphor can be altered to match the xenon spectrum. Or the optical conditioner may be modified to match the xenon spectrum. It is also possible to use one set of LED lights for color measurement and another set of LED lights for trash measurement.

Additional Considerations

There are still two other challenges with utilizing LEDs: beam angle and uniformity. LEDs typically have a different beam angle as compared to a xenon light source. While this may seem as non-critical, it does impact the color measurement. One solution is to utilize optical beam shaping devices (e.g., using optical components such as lenses) to shape the output of the LEDs to match a xenon source. Additional beam shaping devices may also be incorporated to create an LED-based illumination uniformity that is similar to that of a xenon source, as measured at the surface of the sample.

The beam shaping optics can take many forms, and be used in many forms. For example, a single LED is a small light source as opposed to a xenon bulb, which is a relatively long light source. In some embodiments, optics are used to make the output of the LED light source (whether it be one or many LED devices) have a similar long pattern as a xenon bulb. In another embodiment, the beam angle of the LED light source, as compared to the xenon light source, is narrower, and optics are used to change the beam angle of the LED light source to another desired angle, such as would be emitted by a xenon light source. Some embodiments adjust the uniformity of the LED light source as received at the sample window, to more closely match that as would be exhibited by a xenon light source.

Additional Embodiments

1. White LED+Conditioner+Photodiode (the conditioner causes the LED to match the desired characteristics of the xenon light source).
2. LED+Custom Phosphor+Photodiode (the phosphor causes the LED to match the desired characteristics of the xenon light source).
3. Multiple LEDs, each with different spectral output+Conditioner+Photodiode (Effective summation of multiple LED spectrums match the characteristics of the xenon light source).
4. White or Multiple Spectral LED+Conditioner+Photodiode+Reassignment of the values of the calibration tiles that are used in color matching, such that the color of the cotton will be read correctly.
5. White or Multiple Spectral LED+Conditioner+Photodiode+Correction algorithm.
6. White or Multiple Spectral LED+Spectrometer+Algorithm with Digital Conditioner.
7. LED+Spectrometer+Algorithm with Digital Conditioner.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An apparatus for measuring at least one of color and trash in a fiber sample, the apparatus comprising:
    a light emitting diode light source for generating an incident light that is directed toward the fiber sample, and reflected by the fiber sample, thereby producing a reflected light,
    a sensor for receiving the reflected light and producing a signal,
    a controller for controlling the light source and the sensor, and at least one of receiving and adjusting the signal, and
    means for conditioning at least one of the incident light, the reflected light and the signal to compensate for differences between the light emitting diode light source and a xenon light source.
2. The apparatus of claim 1, wherein the means for conditioning the incident light comprise at least one of a beam shaping device and an optical filter disposed between the light source and the fiber sample.
3. The apparatus of claim 1, wherein the means for conditioning the reflected light comprise at least one optical filter disposed between the fiber sample and the sensor.
4. The apparatus of claim 1, wherein the means for conditioning the signal comprise a digital signal processor.
5. The apparatus of claim 1, wherein the sensor is at least one of a spectrometer, a photomultiplier tube, a photodiode, and a charge-coupled device.
6. The apparatus of claim 1, further comprising at least one reference light emitting diode monitored by the controller for capturing the signal when the at least one reference light emitting diode is at a predetermined brightness.
7. The apparatus of claim 6, wherein the at least one reference light emitting diode is separate and distinct from the light source.
8. The apparatus of claim 6, wherein the at least one reference light emitting diode is part of the light source.
9. The apparatus of claim 6, wherein the at least one reference light emitting diode does not illuminate the fiber sample.
10. The apparatus of claim 6, further comprising means for conditioning light from the at least one reference light emitting diode prior to being sensed.
11. The apparatus of claim 10, comprising first and second reference light emitting diodes monitored by the controller for capturing the signal when the first and second reference light emitting diodes are at predetermined brightnesses, wherein the means for conditioning light from the first and second reference light emitting diodes are configured for separately conditioning light from the first and second reference light emitting diodes prior to being sensed.
12. The apparatus of claim 1, wherein the means for conditioning are settable with different parameters depending at least in part upon whether a color measurement is to be taken or a trash measurement is to be taken.
13. A method for measuring at least one of color and trash in a fiber sample, the method comprising the steps of:
    using a light emitting diode light source to generate an incident light that is directed toward the fiber sample, and reflected by the fiber sample, thereby producing a reflected light, receiving the reflected light and producing a signal with a sensor,
    controlling the light source and the sensor, and at least one of receiving and adjusting the signal, and
    conditioning at least one of the incident light, the reflected light and the signal to compensate for differences between the light emitting diode light source and a xenon light source.
14. The method of claim 13, wherein the incident light is conditioned using at least one beam shaping device and/or at least one optical filter disposed between the light source and the fiber sample.
15. The method of claim 13, wherein the reflected light is conditioned using at least one optical filter disposed between the fiber sample and the sensor.
16. The method of claim 13, wherein the signal is conditioned using a digital signal processor.
17. The method of claim 13, wherein the sensor is at least one of a spectrometer, a photomultiplier tube, a photodiode, and a charge-coupled device.
18. The method of claim 13, further comprising monitoring at least one reference light emitting diode with a controller and capturing the signal when the at least one reference light emitting diode is at a predetermined brightness.

19. The method of claim 13, wherein the conditioning is set with different parameters depending at least in part upon whether a color measurement is to be taken or a trash measurement is to be taken.

\* \* \* \* \*